United States Patent
Chandrasekharan et al.

(10) Patent No.: US 9,651,505 B2
(45) Date of Patent: May 16, 2017

(54) METHOD FOR OBTAINING INFORMATION ABOUT A RADIATION SOURCE OR A MATERIAL INTERACTING WITH A RADIATION SOURCE AND A MEASUREMENT SETUP FOR PERFORMING THE METHOD

(75) Inventors: Rico Chandrasekharan, Zurich (CH); Giovanna Davatz, Zurich (CH); Alexander Howard, Zurich (CH)

(73) Assignee: Arktis Radiation Detectors Ltd, Zurich (CH)

( * ) Notice: Subject to any disclaimer, the term of this patent is extended or adjusted under 35 U.S.C. 154(b) by 1067 days.

(21) Appl. No.: 13/806,150

(22) PCT Filed: Jun. 23, 2010

(86) PCT No.: PCT/EP2010/058939
§ 371 (c)(1),
(2), (4) Date: Mar. 11, 2013

(87) PCT Pub. No.: WO2011/160690
PCT Pub. Date: Dec. 29, 2011

(65) Prior Publication Data
US 2013/0204578 A1    Aug. 8, 2013

(51) Int. Cl.
*G01T 3/00*  (2006.01)
*G01N 23/08*  (2006.01)
(Continued)

(52) U.S. Cl.
CPC .............. *G01N 23/08* (2013.01); *G01T 3/00* (2013.01); *G01V 5/0008* (2013.01); *G06F 17/18* (2013.01)

(58) Field of Classification Search
CPC ............ G01N 23/08; G01T 3/00; G06F 17/18
See application file for complete search history.

(56) References Cited

U.S. PATENT DOCUMENTS 3,932,758 A * 1/1976 Burgkhardt ............... G01T 3/00
250/390.03
8,891,720 B2 * 11/2014 Rowland ................... G01T 3/00
376/156
(Continued)

FOREIGN PATENT DOCUMENTS

EP    1847855 A1    10/2007

OTHER PUBLICATIONS

Miller et al., "Contraband Identification in Sealed Containers Using Neutron Transmission", SPIE, 2007, pp. 215-218, vol. 2867.
(Continued)

*Primary Examiner* — Mischita Henson
(74) *Attorney, Agent, or Firm* — The Webb Law Firm (57) ABSTRACT

A method for obtaining information about an unknown neutron source or an unknown material interacting with a known neutron source comprises the steps of: (a) providing a radiation detector capable of delivering a neutron energy information allowing the production of response histogram(s) as a function of neutron energy, (b) measuring with said radiation detector neutrons being emitted from said unknown neutron source or from said unknown material, (c) deriving from said measured neutrons a neutron energy spectrum, especially in form of a histogram, (d) normalizing said energy spectrum or histogram relative to a parameter or set of parameters derived from the measurement of a different variable, (e) comparing said normalized energy spectrum or histogram with known energy spectra or histograms, and (f) drawing conclusions on the basis of said comparison about the nature of the unknown neutron source or unknown material.

19 Claims, 7 Drawing Sheets

(51) Int. Cl.
　　　*G01V 5/00*　　　(2006.01)
　　　*G06F 17/18*　　　(2006.01)

(56) References Cited

U.S. PATENT DOCUMENTS

| | | | | |
|---|---|---|---|---|
| 8,954,300 | B2* | 2/2015 | Scoullar | G01T 1/171 |
| | | | | 703/2 |
| 9,081,100 | B1* | 7/2015 | Bellinger | G01T 3/08 |
| 2006/0289775 | A1* | 12/2006 | Inbar | G01T 1/167 |
| | | | | 250/370.11 |
| 2007/0025505 | A1* | 2/2007 | Bjorkholm | G01N 23/04 |
| | | | | 378/53 |
| 2009/0074128 | A1* | 3/2009 | Bertozzi | G01V 5/0091 |
| | | | | 376/170 |
| 2009/0143923 | A1* | 6/2009 | Breed | G08G 1/205 |
| | | | | 701/1 |
| 2009/0225922 | A1* | 9/2009 | Koltick | H05H 3/06 |
| | | | | 376/159 |
| 2009/0294686 | A1 | 12/2009 | Chandrasekharan | |
| 2010/0006769 | A1* | 1/2010 | Kraft | G01T 1/2907 |
| | | | | 250/370.11 |
| 2013/0204578 | A1* | 8/2013 | Chandrasekharan | G01T 3/00 |
| | | | | 702/180 |
| 2014/0231657 | A1* | 8/2014 | Bolotnikov | G01T 1/17 |
| | | | | 250/370.06 |

OTHER PUBLICATIONS

Eberhardt et al., "Fast neutron radiography scanner for the detection of contraband in air cargo containers", Applied Radiation and Isotopes, 2005, pp. 179-188, vol. 63.

Eberhardt et al., "Fast Neutron and Gamma-Ray Interrogation of Air Cargo Containers", Proceedings of Science, Apr. 2006.

* cited by examiner

METHOD FOR OBTAINING INFORMATION ABOUT A RADIATION SOURCE OR A MATERIAL INTERACTING WITH A RADIATION SOURCE AND A MEASUREMENT SETUP FOR PERFORMING THE METHOD

BACKGROUND OF THE INVENTION

Field of the Invention

Radiation detectors based on noble gas scintillation have the capability of simultaneously detecting gamma and neutron radiation, and offering methods to discern these. Examples of such radiation detectors are disclosed in former patent application US 2009294686, the disclosure of which is fully incorporated into the present application. In particular, such detectors using Helium gas as a detection medium have demonstrated the capability of detecting fast neutrons, delivering an energy deposit spectrum with a straightforward dependence on the energy spectrum of the incoming neutron radiation.

These capabilities are not affected in a statistically significant manner by gamma radiation, as measurements using gamma exposures up to 1 mSv/h from Co-60 sources have shown. Nonetheless, such detectors are capable of clearly quantifying the strength of such gamma exposure by measuring the count rate attributed predominantly to gamma radiation by the detector's mechanisms of gamma rejection.

However, when monitoring for example freight or cargo or containers with unknown contents, it would be extremely helpful to not only detect the presence of a neutron source within said containers, but also obtain information about the individual character of the source.

It is therefore an object of the invention to disclose a method for obtaining information about a radiation source or a material interacting with a radiation source, and a measurement setup for performing the method.

SUMMARY OF THE INVENTION

According to the invention the method for obtaining information about a radiation source or a material interacting with radiation from a radiation source comprises the steps of: (a) providing a radiation detector capable of delivering neutron energy information allowing the production of response histogram(s) as a function of energy, (b) measuring with said radiation detector neutrons being emitted from said radiation source or from said material, (c) deriving from said measured neutrons a neutron energy spectrum, especially in form of a response histogram, (d) normalizing said energy spectrum or response histogram relative to a parameter or set of parameters derived from the measurement of a different variable, (e) comparing said normalized energy spectrum or histogram with known energy spectra or histograms, and (f) drawing conclusions on the basis of said comparison about the nature of the radiation source or material, or both.

According to an embodiment of the invention said known histograms are taken from a database, and said comparing step is made automatically by using a respective comparing means. Such a database may be obtained from simulation or previous measurements.

According to another embodiment of the invention the parameter or set of parameters used for normalization is derived from one or more other measured values introducing an energy dependence into the normalization.

According to another embodiment of the invention the parameter or set of parameters used for normalization is derived from at least one measurement of an intensity of electromagnetic radiation within a predetermined energy range of electromagnetic radiation, such as gamma, infrared, visible or UV radiation.

According to another embodiment of the invention the parameter used for normalization is provided by said radiation detector.

According to another embodiment of the invention said radiation detector is a detector based on He-3, He-4, Ar-40, Xe-131 or an organic scintillation material.

According to another embodiment of the invention said unknown radiation source comprises a plurality of different radiation sources, especially located at different positions in space, and the information gained is used to reject or subtract one or more of said plurality of different radiation sources, especially ambient background radiation, to thereby achieve higher sensitivity for the remaining sources of radiation.

According to another embodiment of the invention said radiation source or said material comprises a nuclear material.

According to another embodiment of the invention further information, especially in form of timing or directional information, is used for drawing conclusions about the nature of the radiation source or material.

According to another embodiment of the invention said energy spectrum or histogram is additionally processed prior to step (e), said additional processing involving a spectral deconvolution, template matching, fitting and/or extrapolation to higher or lower energies based on a set of plausible assumptions.

According to another embodiment of the invention, in step (f), an energy dependent weighting factor is obtained to define the radiation dose of a radiation field for health physics, dosimetric, or monitoring purposes.

According to another embodiment of the invention said conclusions are used for diagnostic purposes in processes involving nuclear fission or fusion.

According to another embodiment of the invention the parameter or set of parameters used for normalization is derived from at least one measurement of a gamma radiation, and there is a gamma source independent of the radiation source.

According to another embodiment of the invention, in step (f), the radiation source is classified as being an industrial source, an alpha-n neutron source, a fission source, a cosmic source, an ambient source, or a specific isotope.

According to another embodiment of the invention the radiation source emits coincident neutrons, gammas or fission fragments from fission decays, and said coincident particles are measured to assess the Poissonian character of said neutron source.

According to another embodiment of the invention said unknown material is placed between the radiation source and the radiation detector, such that the material moderates the neutron radiation.

According to still another embodiment of the invention said material scatters radiation from the radiation source into the radiation detector.

According to another embodiment of the invention a gamma and neutron radiation source as well as gamma and neutron detectors are used, and the information from the detectors is used to gain information regarding an object between the two or in a position where radiation from the source(s) passes through the object prior to arriving at the detector, and said conclusion is drawn from comparing the ratio of detected neutron to detected gamma radiation as a function of energy. In such an embodiment, the sources may be the same or different. Also the detection of gamma radiation may be performed with the same device that is detecting neutron radiation, or with a separate device.

The measurement setup according to the invention comprises: a radiation detector for detecting fast neutron radiation as well as gamma radiation and providing at its output a neutron energy spectrum of the detected fast neutrons and a gamma count rate of the detected gamma radiation or a total count rate as the sum of gamma count rate and other count rates; normalizing means for normalizing the neutron energy spectrum delivered by the radiation detector by means of the gamma count rate or a total count rate as the sum of gamma count rate and other count rates delivered by the radiation detector; and comparing means for comparing the normalized neutron energy spectrum delivered by the normalizing means a known spectrum.

According to an embodiment of the inventive measurement setup the radiation detector uses the scintillation of a noble gas for as a detecting means.

According to another embodiment of the inventive measurement setup the known spectrum for the comparing means is taken from a database which is connected to the comparing means.

BRIEF DESCRIPTION OF THE DRAWINGS

The invention will be explained below on the basis of various embodiments and with reference to the drawings.

DETAILED DESCRIPTION OF THE INVENTION

Figure 1:
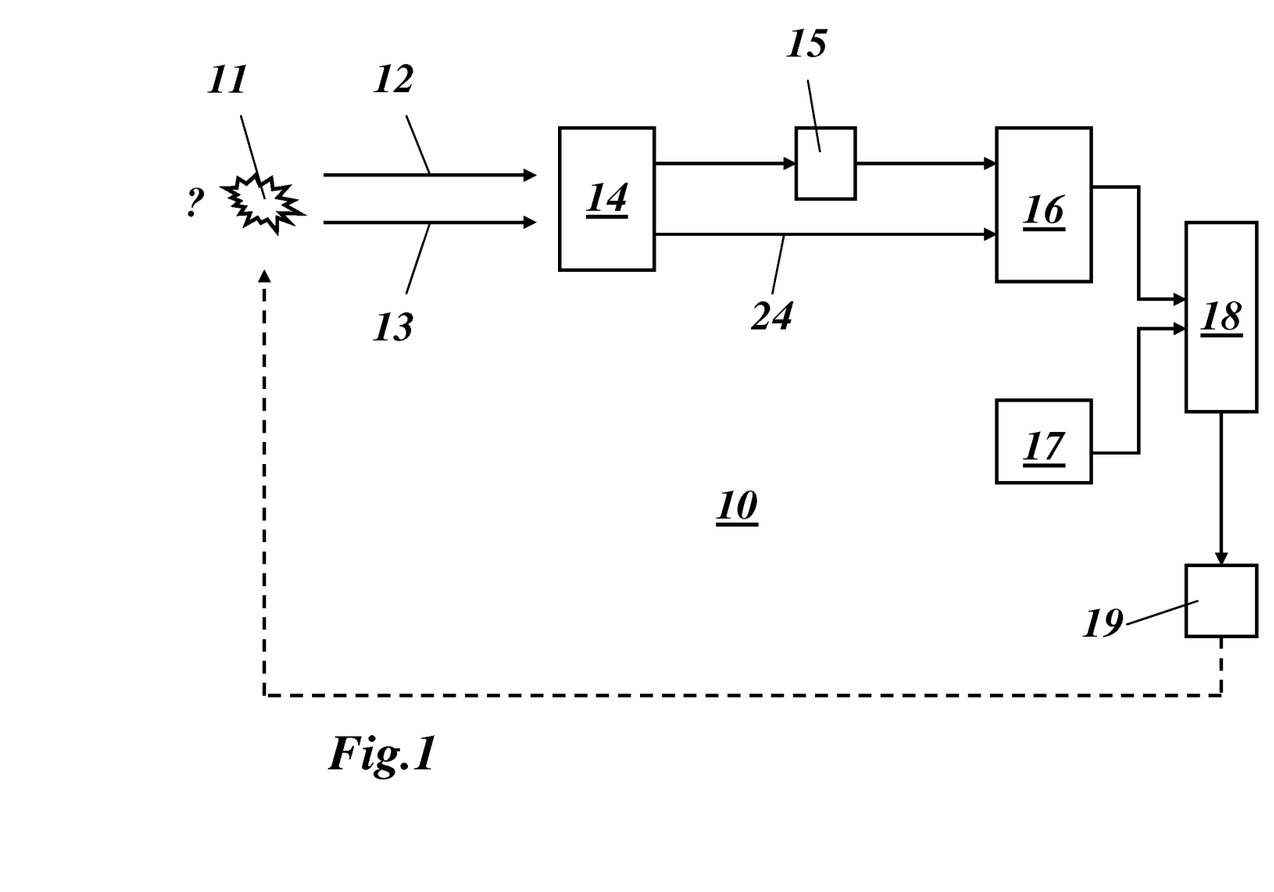
FIG. 1 shows a schematic diagram of a measurement setup in accordance with an embodiment of the invention to measure and characterize the nature of a radiation source.

In a preferred embodiment of the invention, a measurement setup 10 according to FIG. 1 is used. The neutron radiation 12 and gamma radiation 13 emitted by a radiation or neutron source 11 is received with a radiation detector 14. Preferably, a noble gas based scintillation detector is used as the radiation detector 14 to simultaneously perform fast neutron spectral detection and gamma counting. The fast neutron energy spectra 15 are normalized in a normalizing means 16 by an independent parameter. In a preferred embodiment of the invention (FIG. 1) this may be the gamma count rate 24 simultaneously measured by the same radiation detector 14, or the total count measured by the same detector 14. The normalized histograms obtained in this manner will show substantial differences depending on the spectrum of neutron radiation as well as the gamma radiation to which the radiation detector 14 is exposed (see FIG. 2). The comparison of such a normalized measured spectrum in a comparing means 18 with a previously measured or simulated spectrum taken from a database 17 results in information, which is available at an output device 19 and allows assessment of the impinging radiation and characterization of the source.

Figure 2:
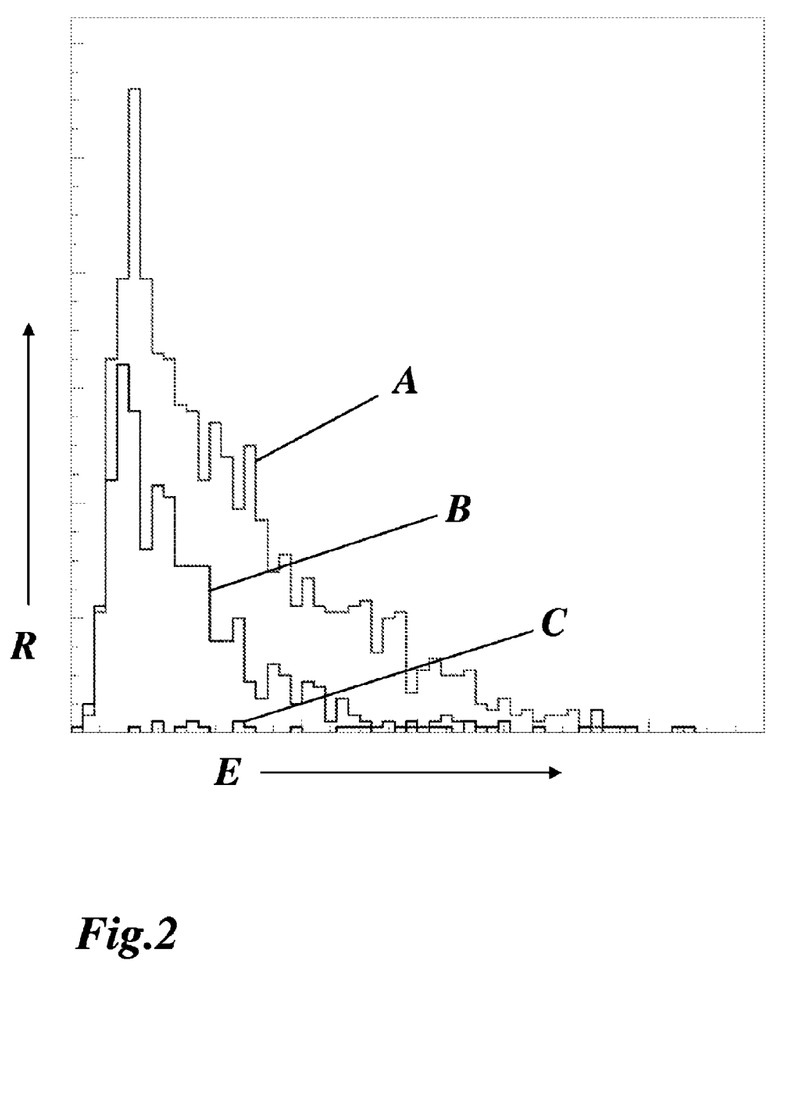
FIG. 2 shows energy dependent detector response curves taken with a measurement setup according to FIG. 1, for three different sources of neutron radiation (curve A: Am Be, curve B: Cf-252, curve C: ambient background)
Figure 3:
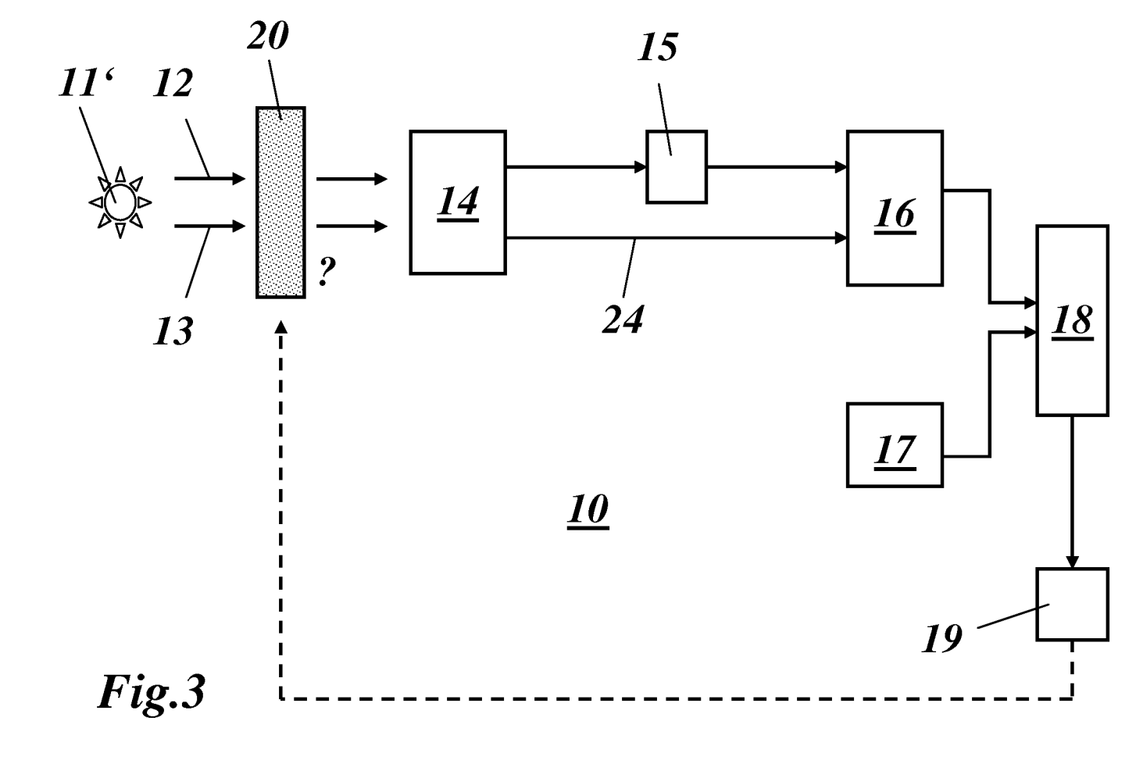
FIG. 3 shows—similar to FIG. 1—a measurement setup to measure and characterize the nature of an unknown material placed between the detector and a known neutron source.
Figure 4:
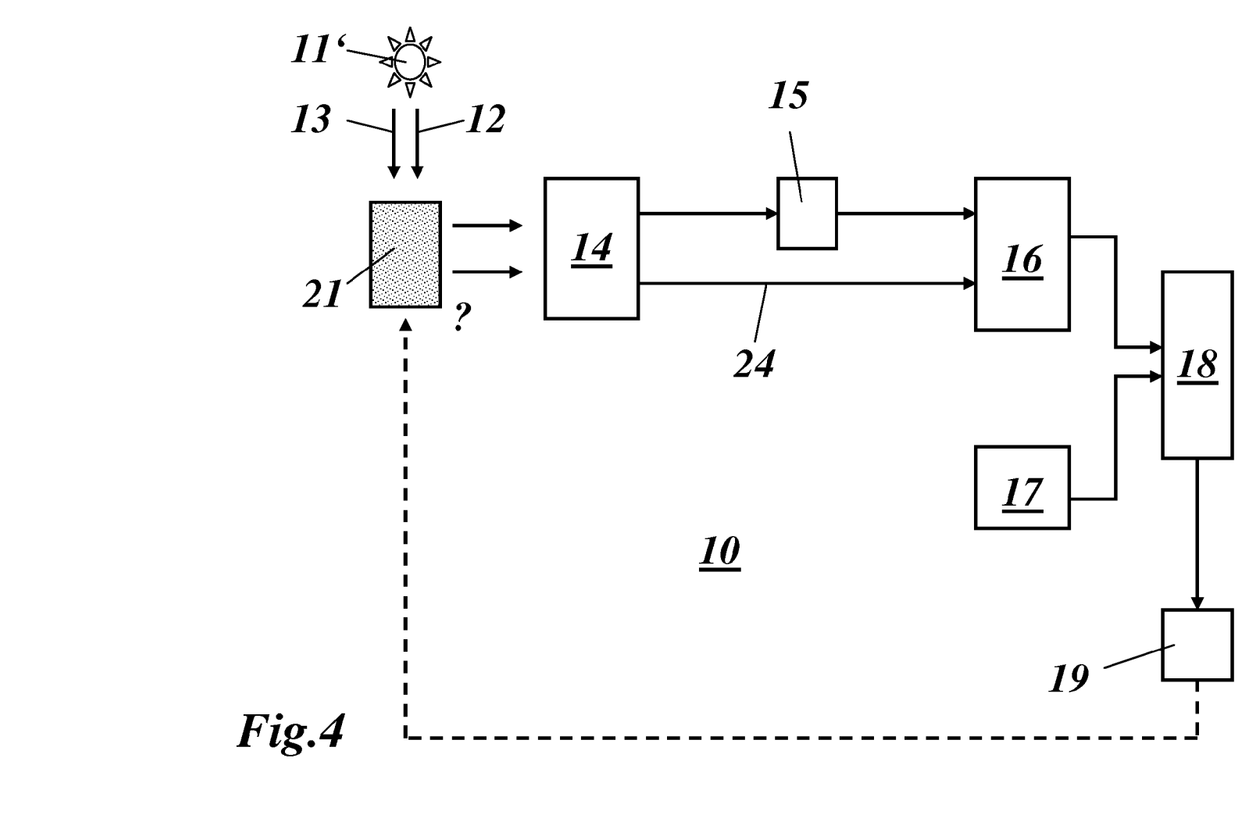
FIG. 4 shows—similar to FIG. 1—a measurement setup to measure and characterize the nature of a material scattering the radiation of a radiation source.
Figure 5:
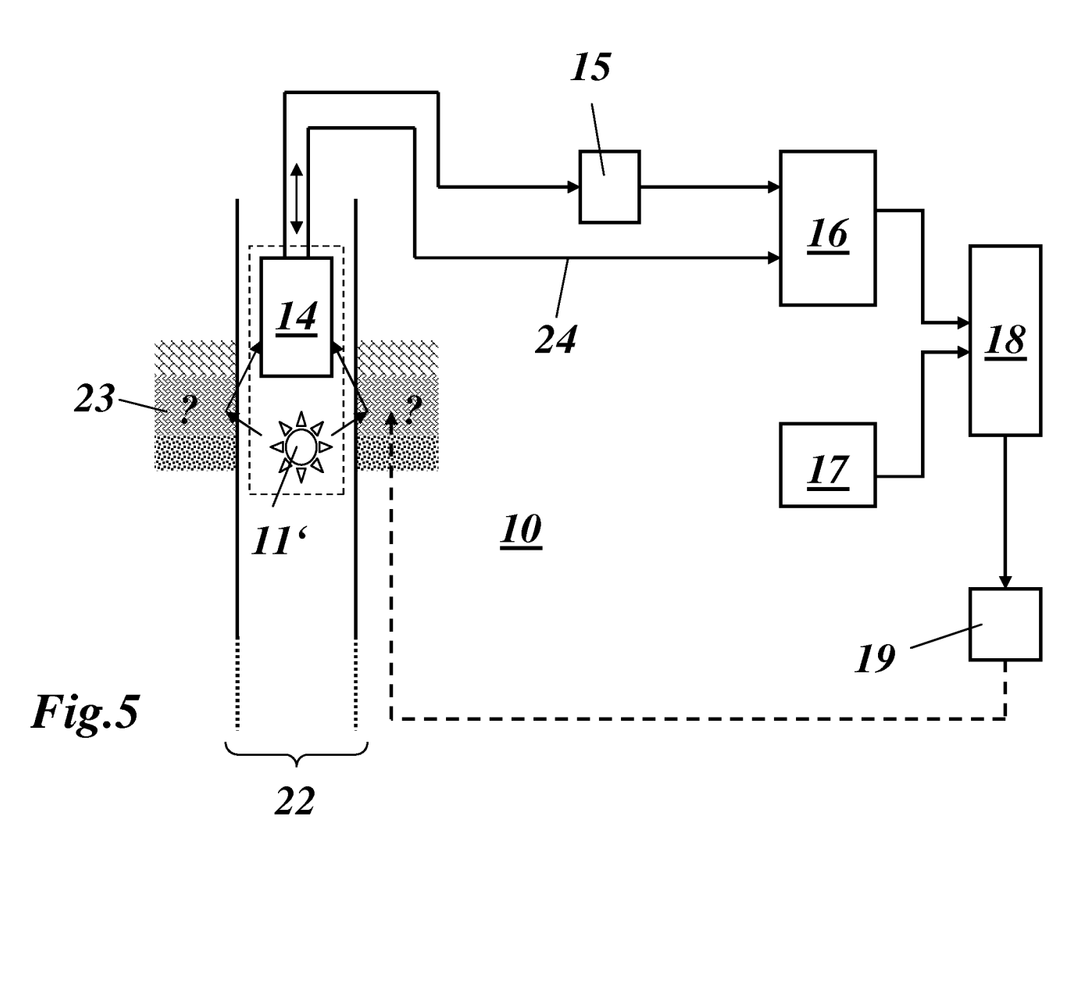
FIG. 5 shows—similar to FIG. 4—a measurement setup to measure and characterize the nature of the material of strata surrounding a well, wherein a radiation source and detector are placed.

The information derived from a measurement according to FIGS. 1 and 2 can then be used to classify or identify the neutron source 11 if so far unknown, or, depending on configuration (see FIG. 3-5), classify or identify unknown materials (20, 21 or 23) between (a known) neutron source 11' and the detector 14, affecting the radiation.

The described method is useful for a number of applications. The most straightforward application of this method is to distinguish between different sources of neutron radiation. Since neutron sources also emit gamma radiation, the normalization parameter(s) in such an embodiment may include a gamma count rate 24, since different neutron sources 11 differ substantially in their gamma emission as well as in their neutron emission. For such applications a radiation detector 14 based on Helium scintillation offers a number of benefits, including the fact that the spectral neutron detection capability is largely unaffected by the gamma radiation typically accompanying the neutron emission.

As measurements show (FIG. 2), the normalized neutron spectra differ significantly for an industrial alpha-n source such as AmBe (curve A in FIG. 2), a fission source such as Cf-252 (curve B in FIG. 2), and ambient neutrons (curve C in FIG. 2). The x-axis relates to the detected neutron's energy E, the normalization of the curves relative to the y-axis is given by the ratio R of detected fast neutrons to detected gamma rays from the respective sources. This allows distinction of the sources on the basis of the shape of the response curve (for example, the shape of the ambient neutron response curve (C) is dramatically different from the shape of the other two response curves A, B, but also on the height of the histogram (for example the AmBe and the Cf-252 response curves A and B have a different height, arising from the different ratios of gamma to neutron radiation). With the same method, a finer categorization according to radioisotope also appears feasible. In another embodiment of the invention, the ratio of detected fast neutrons to total detected radiation may be used for normalization.

In another embodiment of the invention, nuclear materials as for example reactor fuel, nuclear waste, or special nuclear materials are analyzed on the basis of their neutron spectrum. In such an embodiment, coincidently detected neutrons from fission decays could be used as an additional source of information for characterization, especially to assess the Poissonian character of said neutron source.

Figure 6:
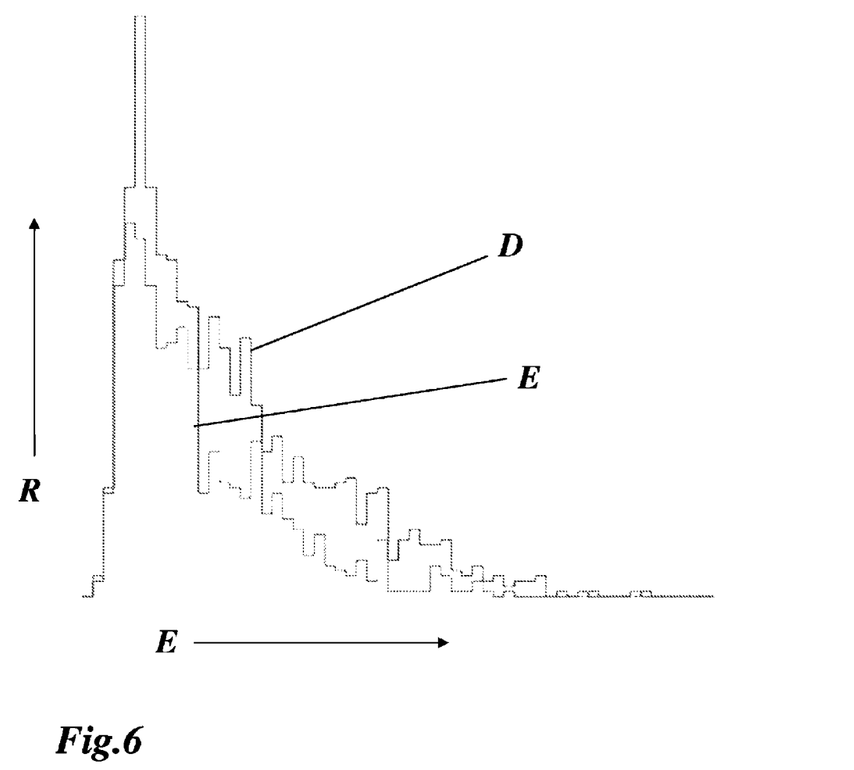
FIG. 6 shows—similar to FIG. 2—energy dependent detector response curves taken with a measurement setup according to FIG. 1 (curve D: unshielded AmBe) and FIG. 3 (curve E: shielded AmBe source)

In a different embodiment of the invention, the method may be used for material analysis. If the radiation on its way from the neutron source 11' to the radiation detector 14 passes through unknown material (20 in FIG. 3; 21 in FIG. 4), the radiation spectra can be altered by interactions with the unknown material 20, 21. For example, if the neutron source 11' is surrounded by neutron moderating material, the resulting normalized histogram will be different than if the radiation is detected more directly. This difference can be exploited to analyze the unknown material 20, 21 in between. Material 20 may for example be a shielding material. FIG. 6 shows—similar to FIG. 2—energy dependent detector response curves (D, E) taken with a measurement setup according to FIG. 1 (curve D: unshielded AmBe) and FIG. 3 (curve E: shielded AmBe source).

A specific example of such an embodiment would be the analysis of the fissionability of a material in a device similar to a well counter. In such an embodiment, the material sample (20 in FIG. 3; 21 in FIG. 4) such as uranium ore, a bulk $UO_2$ sample, high-enriched uranium metals, UAl alloy scraps, LWR pellets, or $^{238}$UTh, is placed in proximity with the radiation detector(s) 14. In a passive mode, radiation emitted spontaneously by the sample is detected to analyze the sample. In an active mode, a separate radiation source such as for example AmLi can be used to interrogate the sample.

In an embodiment of this invention, the technique is used to differentiate known or unknown neutron sources 11' surrounded by different forms of shielding, such as for example polyethylene, cadmium, or lead.

In another embodiment of the invention, this effect is put to use in down-hole well-logging (FIG. 5), where neutron radiation from a neutron source 11' placed in the well 22 is scattered to a down-hole radiation detector 14 of the described properties. In such an embodiment, the normalization parameter(s) may be obtained by measuring gamma or other radiation from the ambient strata 23 or from a down-hole source 14. The normalized histograms allow analysis of the ambient strata 23, for example to measure porosity or hydrocarbon content.

Another embodiment of the invention is an active analysis method with certain parallels to the method of fast neutron gamma radiography (FNGR; see for example "Fast Neutron and Gamma-Ray Interrogation of Air Cargo Containers", J. E. Eberhardt et al., Proceedings of Science, 2006). The FNGR method irradiates an object with gamma and neutron radiation and measures the transmitted gamma and neutron radiation. The ratio of the intensities of the detected radiation is used to assess density and material composition. An embodiment of this invention offers a further dimension to the FNGR analysis method by delivering energy dependent ratios, and thus an additional information dimension.

Figure 7:
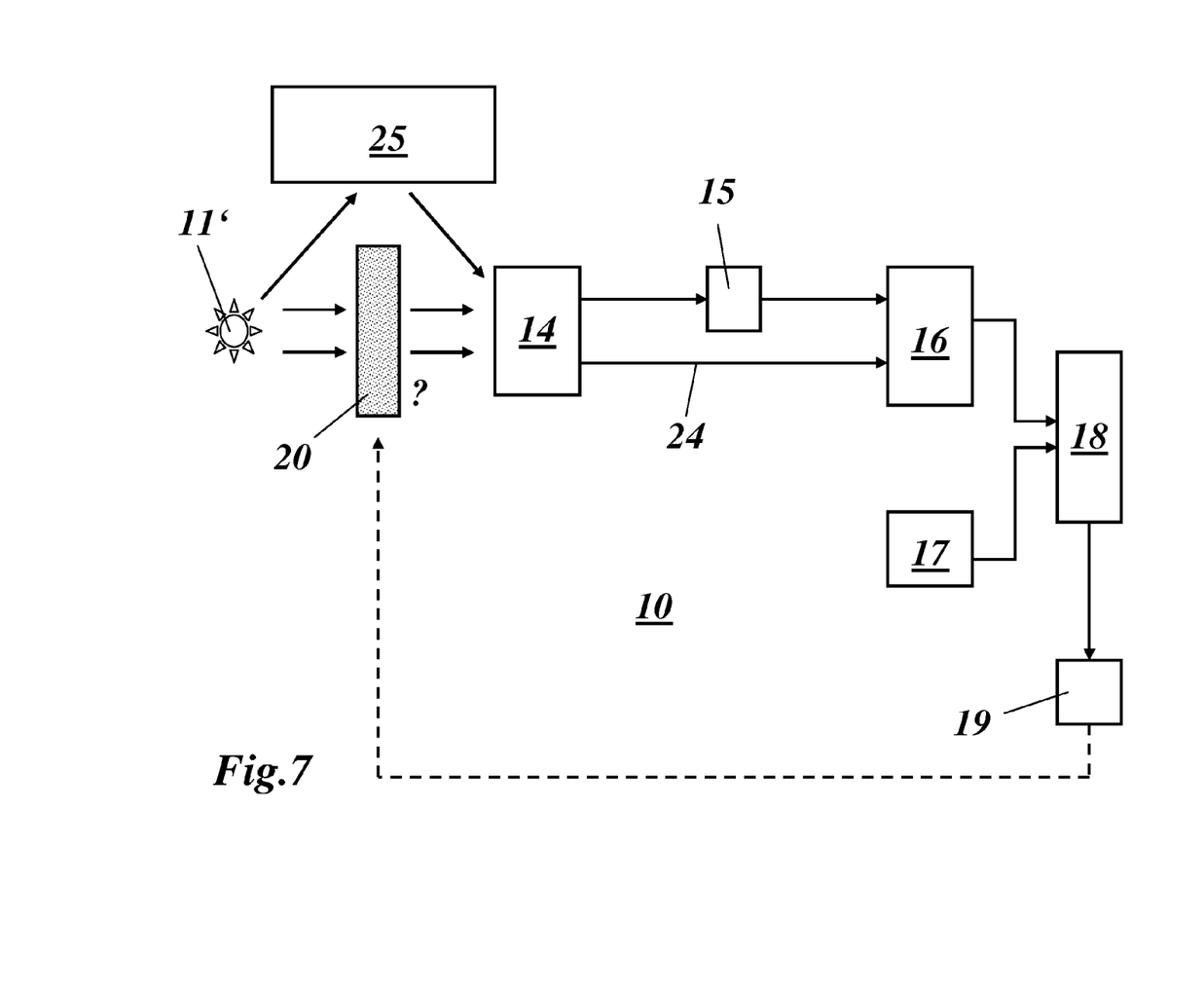
FIG. 7 shows—similar to FIG. 3—a measurement setup to measure and characterize the nature of a material placed between the detector and a source, wherein the material attenuates at least one form of radiation from the source, such that indirect scattering of said form of radiation off other objects contributes significantly to the detection of said form of radiation.

Another embodiment of the invention takes into account that the radiation used for interrogation can cause secondary emission of radiation, in particular of neutrons. This radiation can be distinguished from the interrogating radiation to provide further information about the interrogated material. FIG. 7 shows—similar to FIG. 3—a measurement setup to measure and characterize the nature of a material placed between the detector 14 and a source 11', wherein the material 20 attenuates at least one form of radiation from the source 11', such that indirect scattering of said form of radiation off another scattering object 25 contributes significantly to the detection of said form of radiation.

LIST OF REFERENCE NUMERALS 10 measurement setup
11,11' neutron source
12 neutron radiation
13 gamma radiation
14 radiation detector
15 neutron energy spectrum
16 normalizing means
17 database
18 comparing means
19 output device
20,21 unknown material
22 well
23 stratum
24 gamma count rate
25 scattering object
A,B,C,D,E curve
E energy (a.u.)
R neutron/gamma ratio

The invention claimed is:

1. A method for obtaining information about a radiation source or a material interacting with radiation from a radiation source, said method comprising:
    providing a detector capable of detecting both neutrons and electromagnetic radiation, the detector comprising separate outputs for a neutron energy spectrum of measured neutrons and for an intensity of electromagnetic radiation;
    providing a normalization device comprising two separate inputs, a first input for the neutron energy spectrum and a second input for the electromagnetic radiation, and a single output for a normalized energy spectrum;
    providing a database comprising a previously measured or simulated energy spectrum;
    providing a comparing device with two separate inputs, a first input for the normalized energy spectrum and a second input of the energy spectrum from the database, and a single output for information obtained from comparing the normalized energy spectrum with the energy spectrum from the database;
    measuring with the detector neutrons being emitted from the radiation source or from a material interacting with radiation from a radiation source;
    deriving a neutron energy spectrum from the measured neutrons;
    measuring an intensity of electromagnetic radiation within a predetermined energy range of the electromagnetic radiation;
    deriving a parameter or a set of parameters used for normalization from the measurement of intensity of electromagnetic radiation, thereby introducing an energy dependence into the normalization;
    normalizing the neutron energy spectrum relative to the parameter or set of parameters;
    comparing the normalized energy spectrum with the previously measured or simulated energy spectrum from the database; and
    outputting the information obtained from comparing the normalized energy spectrum with the energy spectrum from the database to an output device.

2. The method according to claim 1, wherein comparing the normalized energy spectrum with the previously measured or simulated energy spectrum from the database is performed automatically by the comparing device.

3. The method according to claim 1, wherein the electromagnetic radiation comprises one or more of gamma, infrared, visible, and UV radiation.

4. The method according to claim 1, wherein the detector is a radiation detector based on He-3, He-4, Ar-40, Xe-131 or an organic scintillation material.

5. The method according to claim 1, wherein said radiation source comprises a plurality of different radiation sources, and the information gained is used to reject or subtract one or more of said plurality of different radiation sources, to thereby achieve higher sensitivity for the remaining sources of radiation.

6. The method according to claim 1, wherein said radiation source or said material comprises a nuclear material.

7. The method according to claim 1, further comprising using the information obtained from comparing the normalized energy spectrum with the energy spectrum from the database for drawing conclusions about the nature of the radiation source or material.

8. The method according to claim 1, wherein normalizing the neutron energy spectrum relative to the parameter or set of parameters comprises using one or more of a spectral deconvolution, template matching, fitting and/or extrapolation to higher or lower energies based on a set of plausible assumptions.

9. The method according to claim 1, wherein the output information is used for diagnostic purposes in processes involving nuclear fission or fusion.

10. The method according to claim 3, wherein the parameter or set of parameters used for normalization is derived from at least one measurement of gamma radiation, and there is a gamma source independent of the radiation source.

11. The method according to claim 1, wherein the output information includes classifying the radiation source as being an industrial source, an alpha-n neutron source, a fission source, a cosmic source, an ambient source, or a specific isotope.

12. The method according to claim 1, wherein the radiation source emits coincident particles including neutrons, gammas or fission fragments from fission decays, and said coincident particles are measured to assess the Poissonian character of said neutron source.

13. The method according to claim 1, wherein said material is placed between the radiation source and the radiation detector, such that the material moderates the neutron radiation.

14. The method according to claim 1, wherein said material scatters radiation from the radiation source into the radiation detector.

15. The method according to claim 1, wherein a gamma and neutron radiation source as well as gamma and neutron detectors are used, and the information from the detectors is used to gain information regarding an object between the source and the detector or in a position where radiation from the source passes through the object prior to arriving at the detector, and the output information is based on comparing a ratio of detected neutron to detected gamma radiation as a function of energy.

16. A measurement setup for performing the method according to claim 1, comprising:
the detector for detecting both neutrons and electromagnetic radiation, the detector comprising separate outputs for a neutron energy spectrum of the measured neutrons and for an intensity of electromagnetic radiation, the detector being capable of detecting both fast neutron radiation and gamma radiation;
the normalization device for normalizing the neutron energy spectrum by means of the gamma count rate or total count rate as the sum of gamma count rate and other count rates delivered by the detector, the normalization device comprising two separate inputs, a first input for the neutron energy spectrum and a second input for the electromagnetic radiation and a single output for a normalized energy spectrum; and
the comparing device for comparing the normalized neutron energy spectrum with the previously measured or simulated energy spectrum from the database, the comparing device comprising two separate inputs, a first input for the normalized energy spectrum and a second input of the energy spectrum from the database, and a single output for information obtained from comparing the normalized energy spectrum with the energy spectrum from the database.

17. The measurement setup according to claim 16, wherein the detector uses the scintillation of a noble gas as a detecting means.

18. The measurement setup according to claim 16, wherein the database is connected to the comparing device.

19. The method according to claim 7, wherein drawing conclusions about the nature of the radiation source or material is based, at least in part, on information in a form of timing or directional information.

* * * * *